(12) United States Patent
Emmert et al.

(10) Patent No.: US 6,474,694 B1
(45) Date of Patent: Nov. 5, 2002

(54) MEDICAL TEST FORM

(75) Inventors: David R. Emmert, Angola, IN (US); Daniel P. Ratka, Williamsville, NY (US); Nikki Phillips, Overland Park, KS (US)

(73) Assignee: Moore North America, Inc., Stamford, CT (US)

( * ) Notice: Subject to any disclaimer, the term of this patent is extended or adjusted under 35 U.S.C. 154(b) by 0 days.

(21) Appl. No.: 09/873,301

(22) Filed: Jun. 5, 2001

(51) Int. Cl.[7] .................................................. B41L 1/26
(52) U.S. Cl. ........................... 283/56; 462/6; 283/66.1; 283/61; 283/900; 283/74
(58) Field of Search ............................ 283/74, 79, 900, 283/61, 105, 101, 62, 56, 66.1; 462/22, 24, 28, 6; 206/232, 461

(56) References Cited

U.S. PATENT DOCUMENTS

| | | |
|---|---|---|
| 3,996,006 A | 12/1976 | Pagano |
| 4,122,947 A | 10/1978 | Falla |
| 4,225,557 A | 9/1980 | Hartl et al. |
| 4,365,970 A | 12/1982 | Lawrence et al. |
| 4,742,002 A | 5/1988 | Guadagno |
| 4,777,964 A | 10/1988 | Briggs et al. |
| 4,789,629 A | 12/1988 | Baker et al. |
| 4,805,773 A | * 2/1989 | Sabongi ........................ 206/489 |
| 4,979,515 A | 12/1990 | Briggs et al. |
| 5,081,040 A | 1/1992 | Patel et al. |
| 5,100,619 A | 3/1992 | Baker et al. |
| 5,119,952 A | 6/1992 | Warriner, Jr. |
| 5,178,419 A | 1/1993 | Bolnick et al. |
| 5,182,191 A | 1/1993 | Fan et al. |
| 5,190,049 A | 3/1993 | Briggs et al. |
| 5,195,123 A | 3/1993 | Clement |
| 5,273,888 A | 12/1993 | Guadagno |
| 5,346,739 A | 9/1994 | Nassoiy |
| 5,612,870 A | 3/1997 | Wellner |
| 5,633,071 A | 5/1997 | Murphy |
| 5,747,344 A | 5/1998 | Cleator |
| 5,773,386 A | 6/1998 | Langan |
| 5,855,395 A | 1/1999 | Foote et al. |
| 5,908,208 A | 6/1999 | Lapsker |
| 5,948,687 A | 9/1999 | Cleator |
| 5,954,369 A | 9/1999 | Seabrook |
| 5,978,466 A | 11/1999 | Quattrocchi |
| 6,007,104 A | 12/1999 | Draper |
| 6,014,438 A | 1/2000 | Quattrocchi |
| 6,016,345 A | 1/2000 | Quattrocchi |
| 6,152,493 A | 11/2000 | Draper |

* cited by examiner

*Primary Examiner*—William Fridie, Jr
(74) *Attorney, Agent, or Firm*—Nixon & Vanderhye PC (57) ABSTRACT

A medical test form having a biological sample receiving material mounted thereto. In one embodiment, the sample receiving material is incorporated in a sample receiving sub-assembly that is secured to a multi-panel carrier substrate that has instructions and/or patient information printed thereon. In another embodiment, the sample receiving material provided on one panel of a V-fold mailer. If necessary or desirable one or more additional panels can be secured to the panels of the V-fold mailer.

17 Claims, 9 Drawing Sheets

MEDICAL TEST FORM

BACKGROUND AND SUMMARY OF THE INVENTION

The present invention relates to medical testing and more specifically to a form for facilitating sample collection and transmission for medical testing.

With recent technological improvements, it is possible to perform biological testing not only on dry biological materials, but with smaller and smaller biological samples. These technological improvements have allowed the development of increasing numbers of home test kits and commercial test kits alike. In the former case, the patient will collect a biological sample in the privacy of their own home or office and transmit the biological sample to a medical testing facility. In the latter case, small or remotely located medical facilities can collect the patient sample and transmit it to the testing facility.

The present invention provides a medical testing device and more specifically a sample receiving device provided as a form-type assembly to facilitate the collection of a biological sample and transmission of the same to a remote facility.

More specifically, the invention is embodied in a medical test form comprising a sample carrier assembly having a sample receiving material secured to a first surface thereof, the sample carrier assembly including a back panel for covering a back surface of said sample receiving material and further including a protective sheet hingedly coupled to the back panel for selectively overlying a top surface of the sample receiving material whereby said sample receiving material is selectively sandwiched between and protected by said protective sheet and said back panel.

According to a first implementation of the invention, the biological sample receiving portion of the medical testing device is provided as a sample receiving sub-assembly that is itself secured to a carrier substrate for transport to the medical facility for testing. The biological sample receiving sub-assembly desirably includes a backing member and a cover member for sandwiching therebetween a biological sample receiving material. Access openings are suitably provided at least in the cover member to allow a sample to be applied to or deposited on the sample receiving material. In an exemplary embodiment, e.g., where the material being sampled is blood, both the cover member and the backing member include aligned openings to facilitate removal of the sample bearing portion of the sample receiving material at the medical testing facility. To protect the sample receiving material prior to the application of the biological sample, to maintain the same contaminant free, a top protective layer is preferably further disposed over the cover member of the sample receiving sub-assembly, thereby to define the protective layer of the assembly. As mentioned above, the biological sample receiving sub-assembly is secured to a carrier substrate, which in a preferred embodiment of the invention is one panel of a multi panel form that includes instructional material and/or patient identifying information.

In an alternate implementation of the invention, the sample receiving material is secured directly to the carrier substrate. More preferably, the carrier substrate includes a two panel V-fold mailer and the sample receiving material is secured to one panel of the mailer. In this embodiment, at least a portion of the carrier substrate is preferably transparent to permit visualization of the sample receiving material therethrough. The remaining portions of the carrier substrate are preferably formed from a material that may be printed to allow instructional materials and/or patient information to be applied thereto.

The medical test form of the invention may advantageously be used to receive and transport blood samples, but other biological samples may be applied to and transported therewith.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which.

DETAILED DESCRIPTION OF THE INVENTION

Figure 1:
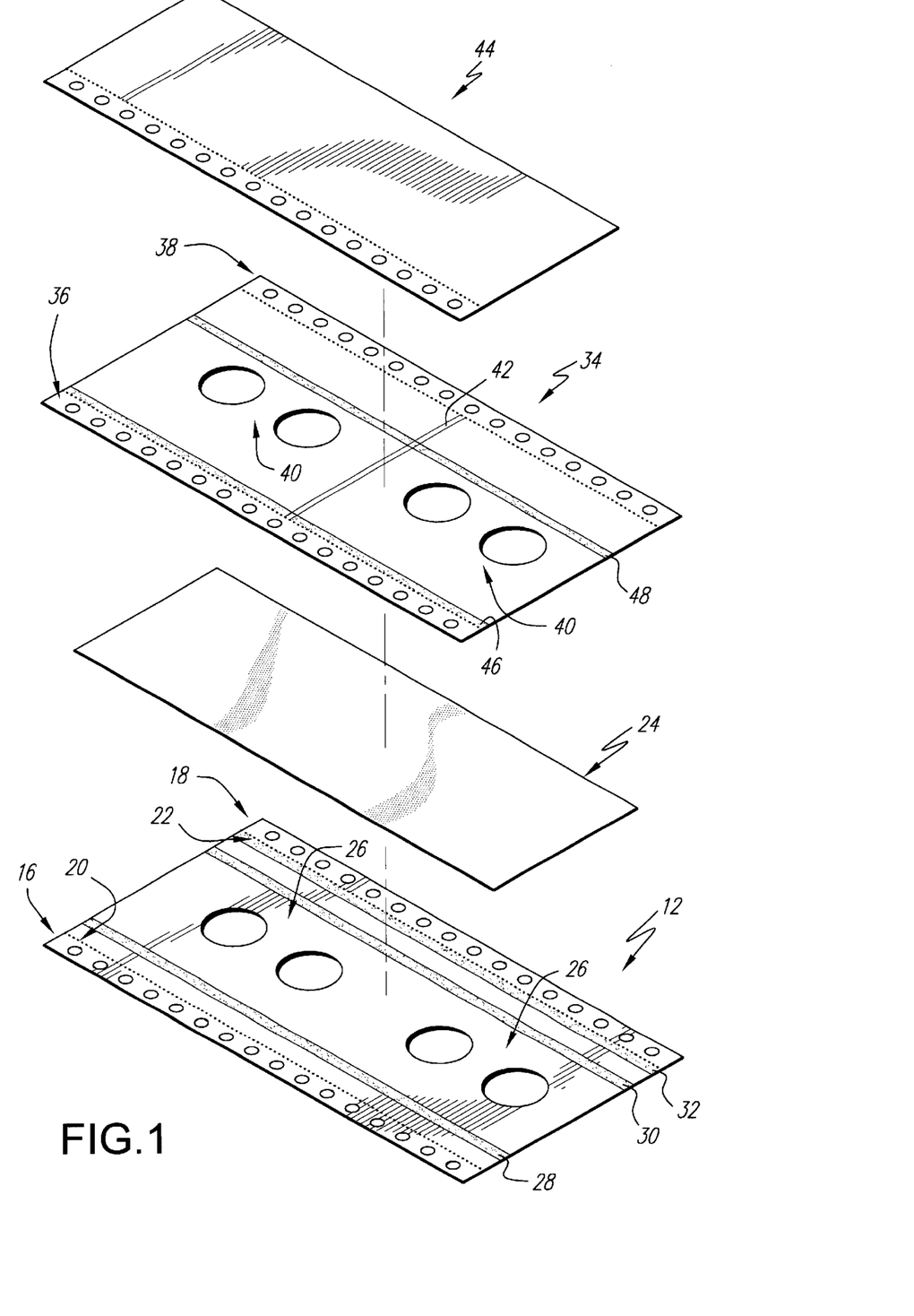
FIG. 1 is an exploded perspective view of a sample receiving sub-assembly according to a first embodiment of the invention.
Figure 3:
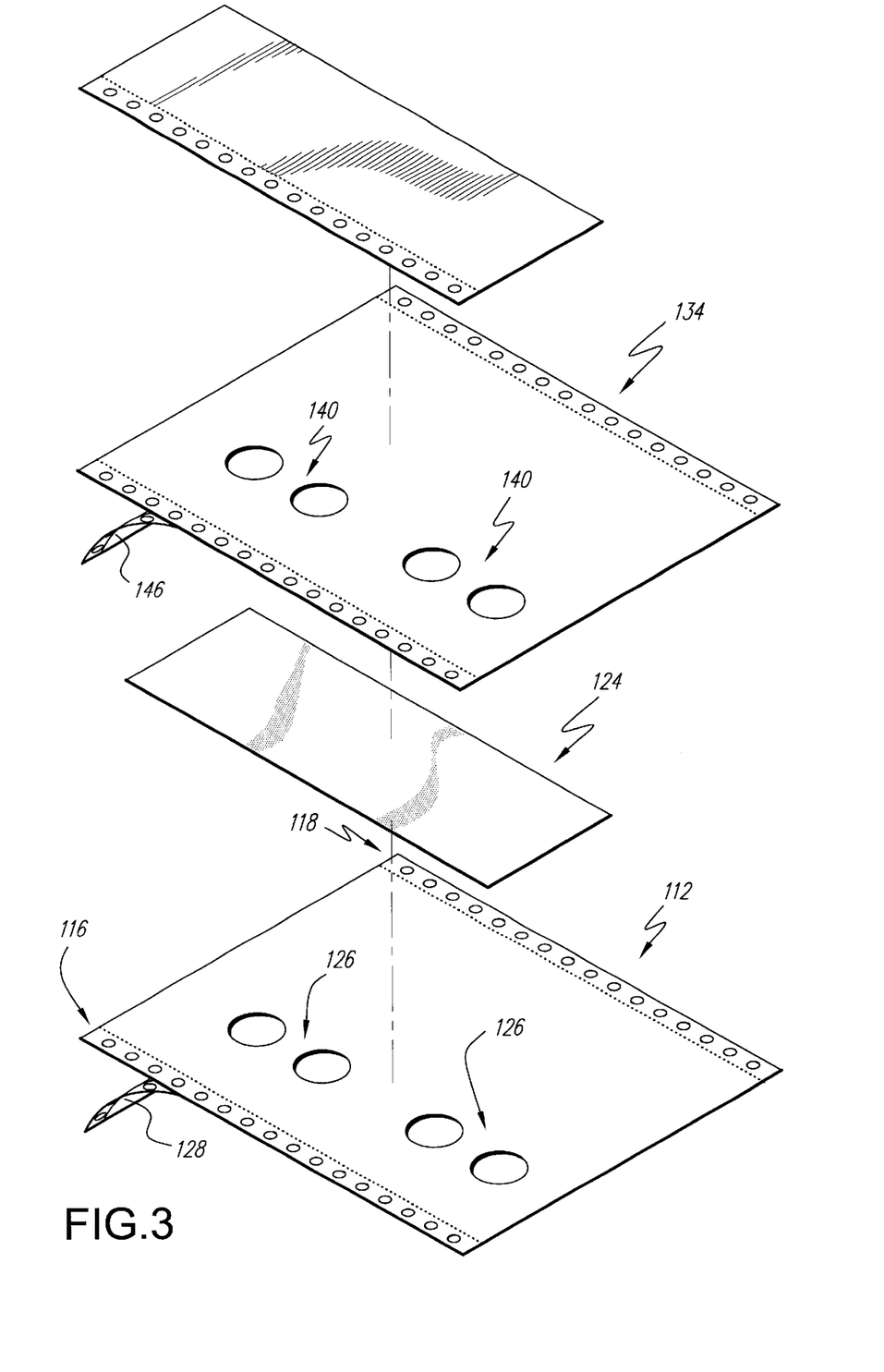
FIG. 3 is an exploded perspective view of a sample receiving sub-assembly according to a second embodiment of the invention.
Figure 4:
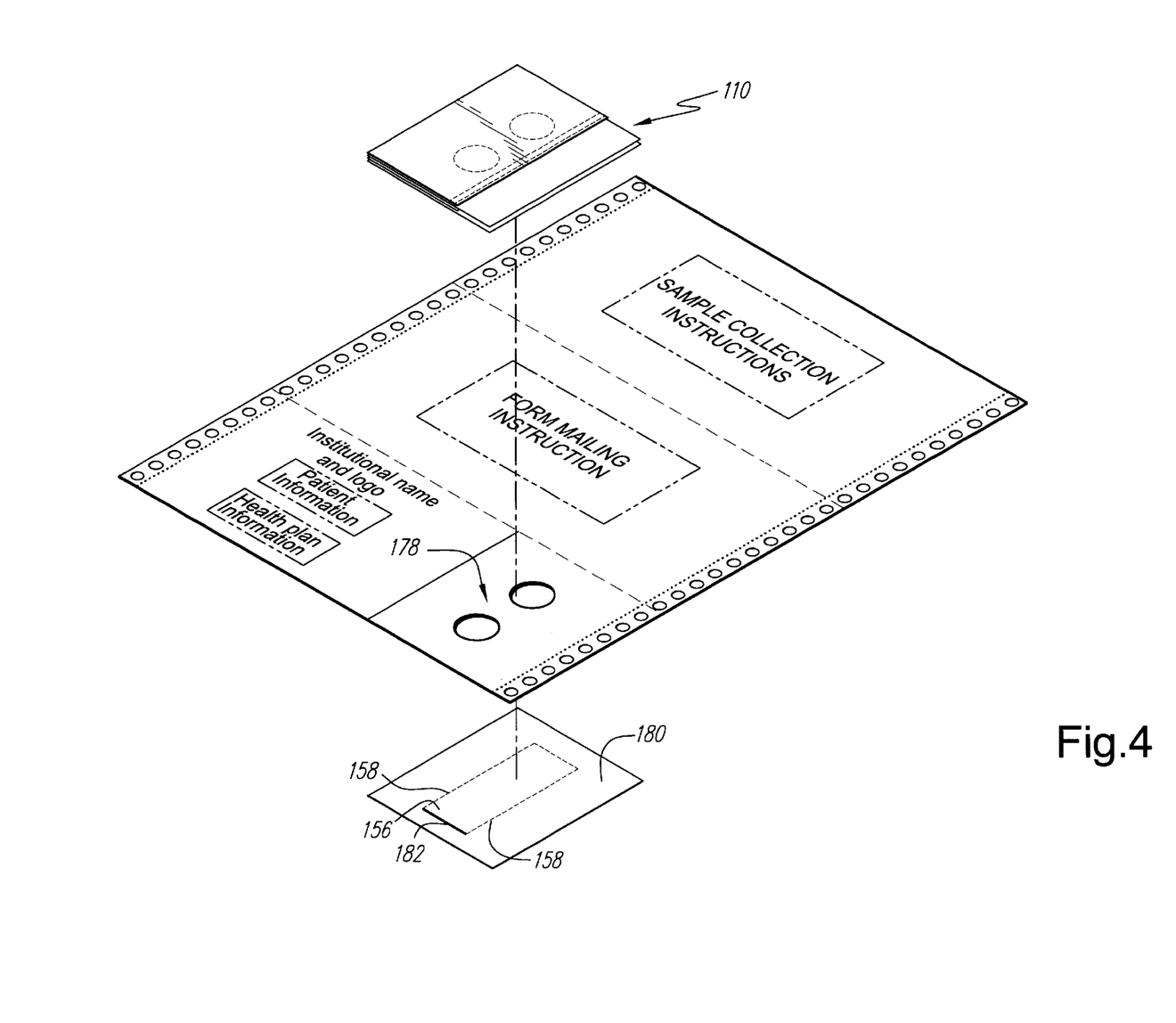
FIG. 4 is an exploded perspective view of a medical test form according to an alternate embodiment of the invention.

Referring to FIGS. 1 and 4, according to a first implementation of the invention, the medical test form of the invention is comprised of a sample receiving sub-assembly and a sample carrier substrate for supporting and transporting the sample receiving sub-assembly first to the patient for sample collection and thereafter to a medical testing facility for examination of the collected biological sample. Two examples of a sample receiving sub-assembly according to the first implementation of the invention are illustrated respectively in FIGS. 1 and 3, it being understood that the illustrated examples are not limiting as to the implementation of the invention.

Referring to the embodiment shown in FIG. 1, the sample receiving sub-assembly 10 includes a bottom layer or backing member 12 which is secured as described in greater detail below to the carrier substrate 14. The material of the backing member may be, for example, 15# paper up to and including a tag material with 18 point tag material being the maximum for presently contemplated processing equipment. In a preferred embodiment, the backing material is 28# OCR or a similar such weight material. As illustrated, in a presently preferred embodiment, to facilitate feed of the stock material for further processing, the backing member 12 is in the form of a continuous web that is provided with first and second lines of sprocket holes 16,18 for facilitating tractor feed of the backing member 12 during assembly, as described in greater detail below. Following assembly of the components of the sample receiving sub-assembly, the edges of the sub-assembly are advantageously removed by feeding the sub-assembly through a slitter. Removal of the edges may be facilitated by providing a perforated line or other line of weakness 20,22 parallel to each side edge. The continuous web is then cut to define discrete sample receiving sub-assemblies 10.

A sample receiving material 24 is provided for sample collection and retention. In an exemplary embodiment, an absorbent blotter material, such as a blood blotter material is provided as the sample receiving material. Suitable such materials are known with an exemplary such absorbent blotter material being made by Schleicher & Schuell.

The backing member 12 is run on an offset web press, for example, with a series of two hole pairs 26 punched all the way through for defining access openings to the sample receiving material 24. Although the illustrated embodiment provides two holes for each sample receiving sub-assembly, it is to be understood that the number, size and disposition of holes depends, for example, on the biological material being sampled, the volume to be applied, and the medical test(s) to be performed. Thus, the illustrated number, size and disposition of holes is considered to be merely an example of how the invention might be adopted.

After the holes are formed, the perforated backing member 12 is then fed through a collator to have glue applied thereto for assembly to the remaining components of the sample receiving sub-assembly. In the illustrated embodiment, three strips of glue 28, 30, 32 are applied to the backing member 12, two glue strips 28,30 being provided for securing the sample receiving material 24 and the third glue strip 32 being provided for adhering a cover member 34, as described in greater detail below. Additional glue strip(s) may be provided, e.g., adjacent the line of weakness 20, to ensure proper adhesion of the sample receiving material 24 and/or cover member 34. The glue applied to the backing member is preferably a non-toxic white glue so as to ensure that there will be no contamination of the sample received and held by the sample receiving material 24. As illustrated, the sample receiving material 24 is applied on top of the backing member 12. A cover member 34 is then applied to the topside of the sample receiving material 24 and the edges are glued down on the backing member 12.

More specifically, a cover member 34 which may be formed from the same material as the backing member 12, or lighter depending upon the customer's specifications is applied on top of the sample receiving material 24 and anchored by the glue provided on the backing member 12. Additional glue may be applied to the backing member 12 and/or sample receiving material 24 as necessary or desirable to laminate the layers together.

To facilitate feed, the cover member 34 is in the form of a web that has marginal sprocket holes 36, 38 to facilitate feed. Further more the cover member web has pairs of holes 40 punched all the way therethrough for being registered with the corresponding holes 26 of the backing member. A score or crush bar 42 is defined at spaced locations along the cover member web, the laminated web assembly being severed there in due course to define discrete sample receiving sub-assemblies 10 for application to a carrier substrate 14, as described below.

A top protective layer 44 is further provided to protect the holes 40 of the cover member 34 and associated sample receiving material 24. The top protective layer 44 can be made of any lightweight material with 17# or 18# being considered appropriate, although even a non-pressure sensitive synthetic will be satisfactory. Glue strips 46,48 are applied to the cover member to hold down the top protective layer 44. Desirably, at least the top right corner of the top protective layer 44 remains free for a finger lift motion. Glue strip 48 may be a material for detachably securing the top protective layer so that the top protective layer can be lifted from the sample openings for the application of a sample and re-adhered to protect the applied sample thereafter. In the alternative, if a permanent-type glue is applied to the cover member, then the top protective layer can be perforated, or the sheet can be peeled from the adhesive but not re-adhered, to facilitate exposure of the sample application holes 40. As noted above, the backing member and cover member are run on an offset web press first to e.g. print registration marks, then punch, then form the marginal holes. A sample receiving sub-assembly web is then created at a collator, where the glue is applied and the components assembled. After the collator, rolls of the sample receiving sub-assembly web are brought to a Tamarack to be put on to the form front as described in greater detail below.

Figure 2:
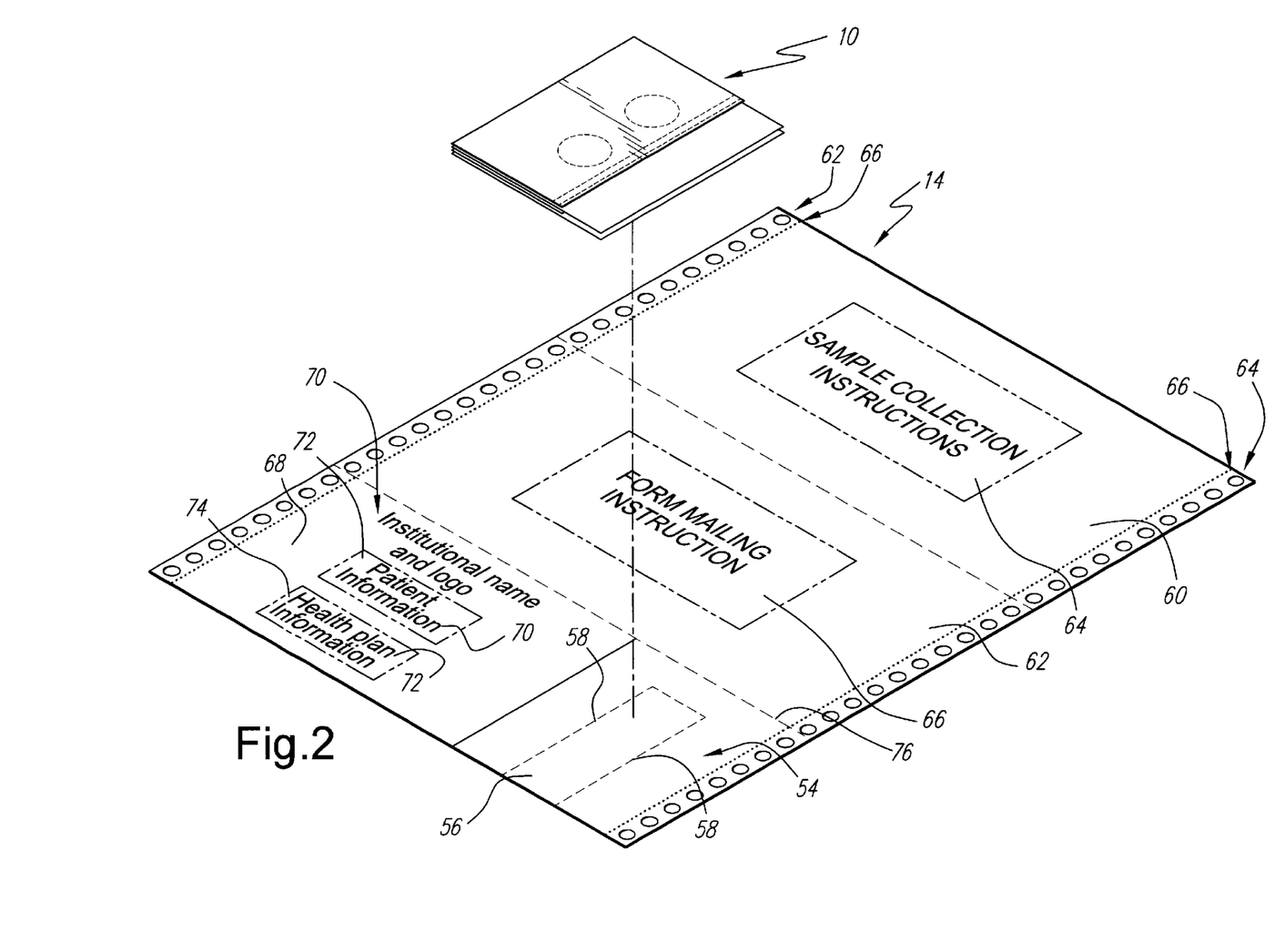
FIG. 2 is an exploded perspective view of a medical test form according to one embodiment of the invention.

A carrier substrate 14 to which a sample receiving sub-assembly 10 formed by assembling and cutting the layers shown in FIG. 1 is applied to define a medical test form is illustrated in FIG. 2. The carrier substrate 14 can be provided as individual sheets, but most preferably the carrier substrate 14 is one segment of a preprinted web along which the carrier substrates are defined end-to-end. Accordingly, the carrier substrate of the illustrated embodiment has marginal tractor feed holes 50,52 defined along each marginal edge thereof for feeding and guiding the same during pre-printing, punching, and sample receiving sub-assembly application. It is to be understood that these marginal portions are preferably removed following assembly and before transmission to the consumer by passing the completed form through a slitter in advance of cutting and stacking, or by other known means such as tearing along preformed perforations.

To secure the sample receiving sub-assembly 10 to the carrier substrate 14 to define a medical test form, adhesive (not shown) is applied to at least a portion of the sub-assembly receiving portion 54 of the form. In the illustrated embodiment, a removable or openable tab 56 is defined by perforation 58 in the sub-assembly receiving portion 54 of the form. The tab 56 is provided so that at the medical testing facility, access can be had to both the front and rear faces of the sample receiving material 24 so that the sample receiving material exposed at the holes 40,26 of the cover and backing members can be removed, as by punching, for further processing independent of the medical test form. Preferably adhesive is not applied to the tab so that it can easily be removed from the backing member. Desirably, a moisture resistant coating (not shown) is applied to at least the tab 56 to prevent undesired bleed through of the liquid sample applied to the sample receiving material 24.

In this example, the carrier substrate 14 is a three-panel form including first and second panels 60,62 which may carry various pre-printed informational materials 64,66 related to the medical test(s) to be carried out. For example, the first panel 60 can include step by step instructions 64 on how to take the required biological sample and apply it to the sample receiving sub-assembly 10, which in the illustrated embodiment is provided on the third panel 68. Further, the second panel 62 may include medical form mailing instructions 66 on how the collected sample is to be forwarded to the medical testing facility. The first or second panel may additionally include areas to be completed by the patient or the other medical provider to record patient related information, date information and the like. Advantageously, a bar code (not shown) is provided on either the first and second panel which corresponds to bar code (not shown) provided on the third, sample receiving sub-assembly carrying panel 68 for identification purposes.

The third sample receiving and transporting panel 54 of the form also includes certain preprinted information such as the institutional name and logo 70, and may include an area 72 for preprinted patent information. One or more additional areas 74 may desirably be provided for supplying health plan information and the like. Area(s) (not shown in particular) may also be provided for the patient to provide additional information or correct preprinted information.

Although in the illustrated embodiment, the sample carrying and transporting panel of the form is provided as the third, bottom panel of the form, the invention is not limited to such a configuration and the sample carrying panel may be disposed at the top of the form or between the other two, informational panels.

To transmit the biological sample to the testing facility, the sample receiving sub-assembly carrying panel 68 is separated from the remaining panels and deposited in an envelope for transmission to the testing facility. To facilitate detachment of the sample bearing panel, adjacent line(s) of weakness, such as perforated line 76, are provided so that the panel 68 can be separated from the remaining panels.

As noted above, the top protective layer that protects the holes 40 and the sample receiving material 24 in advance of sample application can be provided so as to be selectively lifted and re-adhered, or lifted but not re-adhered or removed entirely at the time of sample application. Preferably, the top protective layer is adapted to remain in place and thus is preferably adapted to be re-adhered to protect the sample following application, during detachment of the sample bearing panel 54 and during transport.

As an alternative to defining a tab 56 with perforations 58 in the carrier substrate 14 for providing access to the sample apertures of the sample receiving sub-assembly, holes may be formed in the carrier substrate for registration with the holes 40, 26 of the sample receiving sub-assembly 10, with a tab bearing panel being then applied to the carrier substrate to cover and protect the sample receiving material 34, as described in greater detail below with reference to FIG. 4.

Another embodiment of a sample receiving sub-assembly 110 is illustrated by way of further example in FIGS. 3 and 4. In this embodiment, the backing member web 112 is formed from a paper stock material having a pressure sensitive adhesive on the bottom surface thereof and a liner paper 128 applied thereto to protect the pressure sensitive adhesive before formation of the sample receiving sub-assembly. Thus, the backing material is a pressure sensitive material with holes 126 punched completely therethrough for sample access at the medical facility, as described above. Again, marginal or sprocket holes 116, 118 are formed along the longitudinal edges of the sheet material to facilitate tractor feed. A sample receiving blotter material 124 is disposed on the top face of the backing material 112. In this embodiment, no adhesive has been applied to the top surface of the backing material, as the sample receiving material 134 will be held in place by the cover member 134 as described below.

The cover member 134 generally corresponds in configuration and composition to the backing material 112, comprising a pressure sensitive material with holes 140 dye cut down to the liner 146, or completely therethrough. To form the sample receiving sub-assembly, the liner material 146 is removed from the cover member 134 and the cover member is applied to the sample receiving material 124 disposed on the backing member 112. The adhesive on the bottom face of the cover member 134 will thus hold the sample receiving material 124 in place with respect to the backing member 112 as the respective sheets have been aligned. If pressure sensitive adhesive is applied to and exposed on the entire bottom surface of backing member 112 when the liner 128 is removed then the carrier substrate 114 is desirably provided with holes 178 corresponding in number and disposition to the holes in the sample receiving sub-assembly 110, to facilitate sample bearing material retrieval at the medical facility. As noted above, the number, size and disposition of holes is not limited to the illustrated examples.

In this embodiment, a panel 180, which is detachably secured to the carrier substrate 114 or perforated as at 158 to define an access tab 156, is applied to the undersurface of the carrier substrate 114 to allow selective access to the sample bearing material exposed by apertures 180. As will be apparent from a consideration of the foregoing description, the pre-perforated tabs 56, 156 may be provided in any of a number of configurations, either as a wholly removable tab segment or as a flap type tab which is separated along longitudinal edges, but remains attached to the carrier substrate 14, 114 at one longitudinal end. The other longitudinal end of the tab may extend to the edge of the paper as with the tab 56 shown in FIG. 3 or may be spaced from the carrier substrate edge with a slit 182 being defined to access and open the tab 156, as shown in FIG. 4.

As illustrated furthermore in FIG. 3, a protective top sheet 144 may be included in the sample receiving sub-assembly 110. As in the embodiment of FIGS. 1 and 2, the top sheet 144 is provided for the purpose of keeping any contamination from getting into the holes during the process of mailing the form to the customer and/or to the medical facility. This protective top sheet 144 is most preferably applied during the fabrication of the sample receiving sub-assembly, as shown in FIG. 3, e.g. by being glued on the cover member before the tractor feed margins are severed. In the alternative, however, the protective top sheet may be applied after the sample receiving sub-assembly has been applied to the carrier substrate 114.

Two embodiments of a further alternate implementation of the invention are illustrated in FIGS. 5-9. In these embodiments, the sample receiving material, such as blotter paper, is applied directly to the form on which the sample is transmitted to the medical testing facility. Accordingly, to enclose and protect the sample during transport, the medical test form is preferably composed of at least two panels adapted to be secured together to define a V-fold mailer for transmitting the biological sample to the testing facility. Additional panels may be provided as necessary or desirable, particularly for additional instructional materials for the end user.

Figure 5:
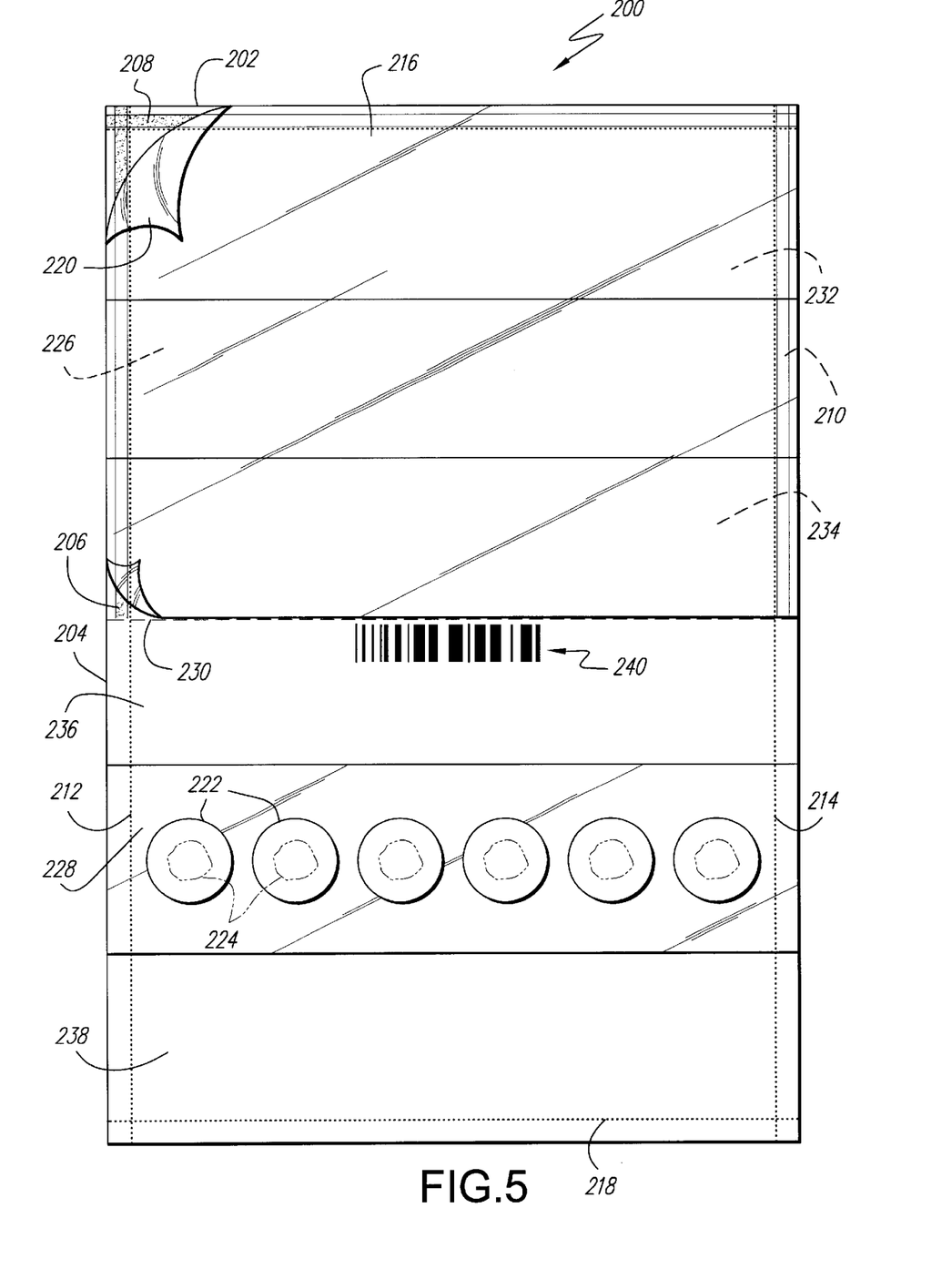
FIG. 5 is a plan view of a medical test form according to a further alternate embodiment of the invention.
Figure 6:
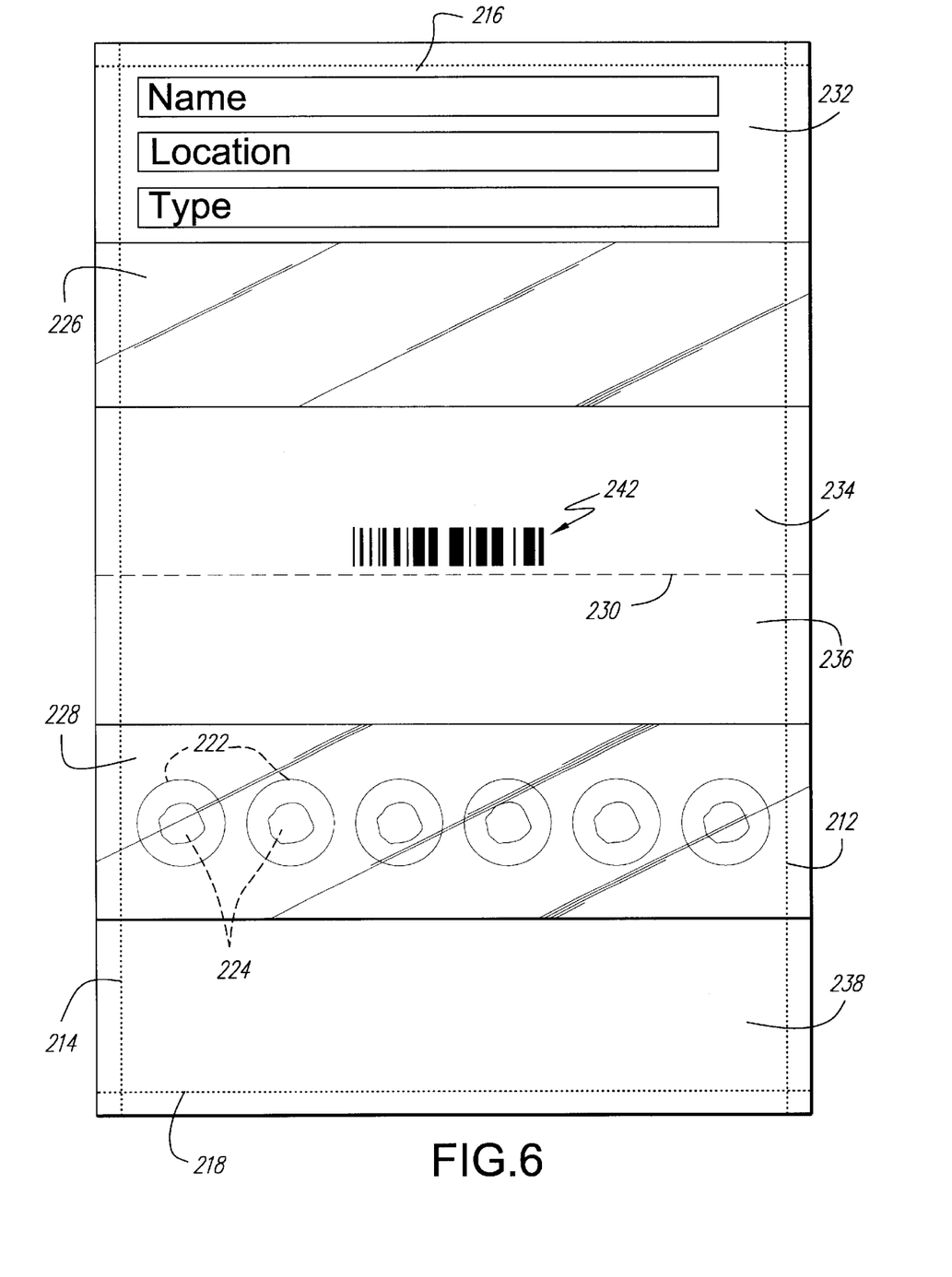
FIG. 6 is a plan view of a second, reverse side of the form shown in FIG. 5.

Referring to FIGS. 5 and 6, in one embodiment the medical test form 200 is comprised of just two panels 202,204, and an adhesive material is provided about at least part of the perimeter of at least one of the two panels for sealing the form for mailing. More specifically, in the embodiment of FIGS. 5 and 6, adhesive strips 206,208,210 are defined about three sides of the first panel 202 of the form. Moreover, perforation lines 212,214,216,218 are provided longitudinally of the form and transversely of the form. This enables the adhered and sealed form to be opened at the medical testing facility by tearing along the aligned perforated lines 212,214,216,218 to open the folded panels and reveal the blotter paper and sample applied thereto. Although generally continuous adhesive bands 206,208,210 are illustrated and preferred to fully seal the biological sample, in some implementations, such as where an outer envelope is provided, it may be deemed sufficient for the adhesive to be discontinuously applied, or applied to only select portion(s) of the perimeter of the panel(s).

In the presently preferred embodiment, the adhesive strips 206,208,210 are pressure sensitive adhesive to facilitate sealing of the test form for transmission to the testing facility. It is to be appreciated that pressure sensitive adhesive is preferred over a rewettable adhesive that must be moistened, because, in general, end users would have an aversion to, e.g., licking the adhesive on a form to which a biological sample was previously applied. To protect the pressure sensitive adhesive prior to sealing the medical form for mailing, a liner material 220 is advantageously applied at least to overlie the adhesive strips and for convenience may be disposed to cover an entirety of the first panel 202 of the V-form mailer, as shown in FIG. 5.

In the illustrated embodiment, the sample receiving material for receiving the biological sample(s) is applied as discrete segments 222 a sample receiving portion of the second panel 204 of the form 200. The discreet sample receiving material segments 222 are respectively adhered to the carrier substrate with glue drops 224 or the like.

The carrier substrate is preferably formed from or coated with a liquid resistant material at least in the vicinity of the sample receiving material segments 222 to contain the sample material. In addition, or in the alternative, the carrier substrate is formed from a plastic substrate that is transparent at least in part to also permit visualization of the sample. Thus, in the illustrated embodiment, at least a portion of the first panel and preferably at least a portion 226,228 of both the first and second panels are transparent plastic in an area corresponding to the area of the form to which the sample receiving material 222 is applied.

Accordingly, when the form is folded about score line 230, the transparent portion 226 of the first panel 202 will overlie the transparent portion 228 of the second panel 204 so that the sample receiving material may be visualized therethrough. Remaining portions 232,234,236,238 of the medical test form are preferably treated or coated on one or both faces so as to enable the printing of patient information and/or instructions thereon. To provide printability, the plastic web may be printed with a laser receptive top coat such as Radcure Rad-Kote 106B-LP to allow information to thereafter be printed thereon. In the alternative, the plastic material may be coated with a thermally sensitive material for thermal printing. As yet a further alternative, a printable media with a pressure sensitive adhesive layer may be applied to selected portions of an otherwise transparent sheet to allow information to be printed or hand written on the form. Additionally, as shown at 240, a bar code is advantageously applied for medical test/patient identification purposes. A corresponding bar code 242 is provided on the outer surface of the test form.

As illustrated in FIG. 6, one or more of the non-transparent regions 232,234,236,238 of the form may be preprinted with test kit identifying or instructional materials. Regions may also be reserved for completion by the patient and/or medical personnel to identify the patient's name, location or address information, insurance information, and the like.

Figure 7:
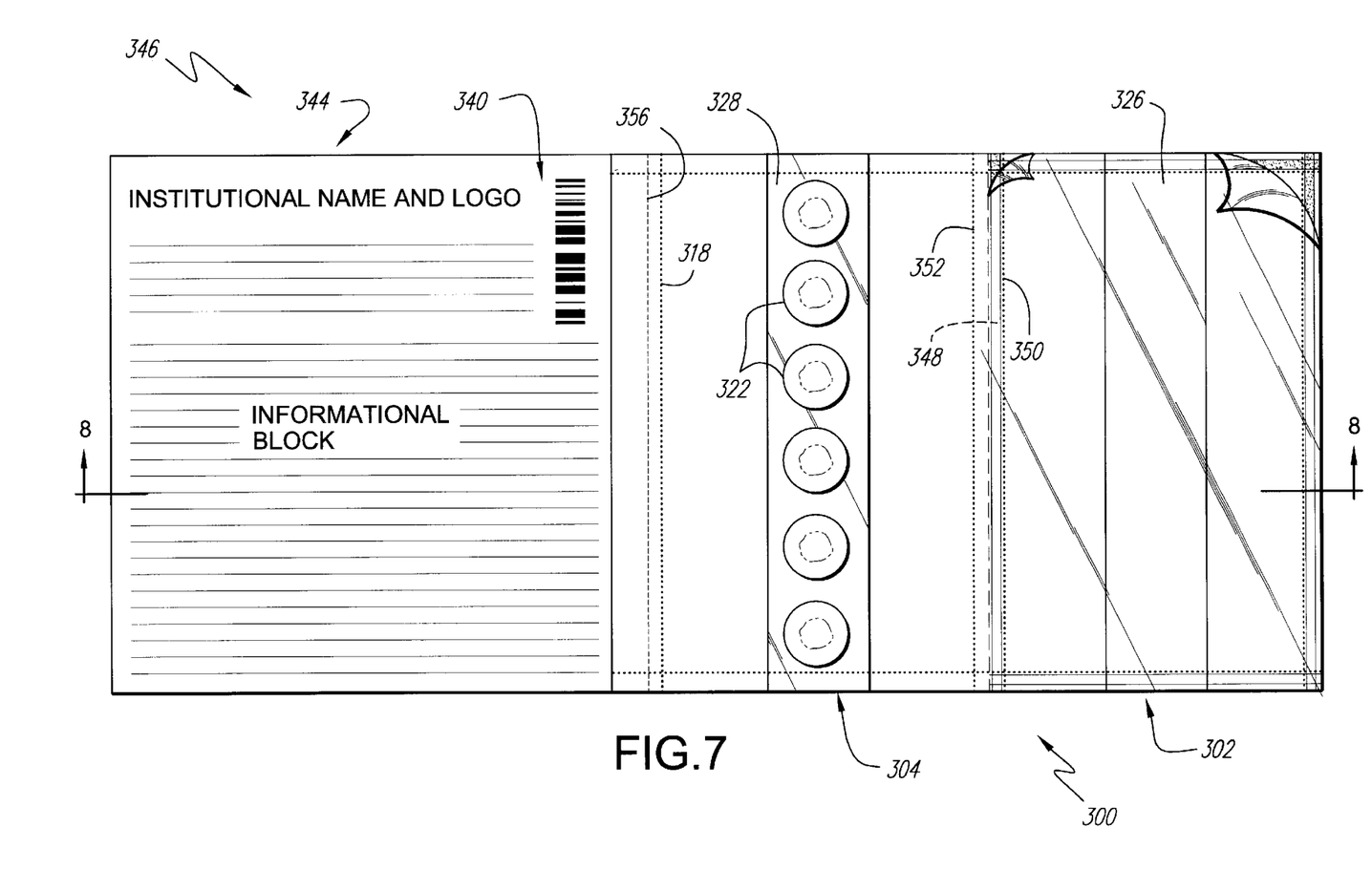
FIG. 7 is a front or inside view of a sample receiving medical test form according to yet a further alternate embodiment of the invention.
Figure 8:
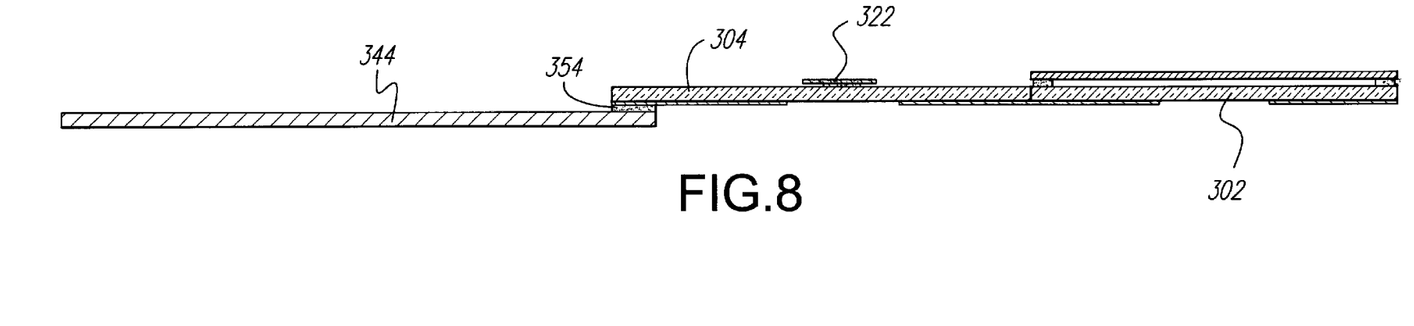
FIG. 8 is a schematic cross sectional view taken along line 8—8 of FIG. 7.
Figure 9:
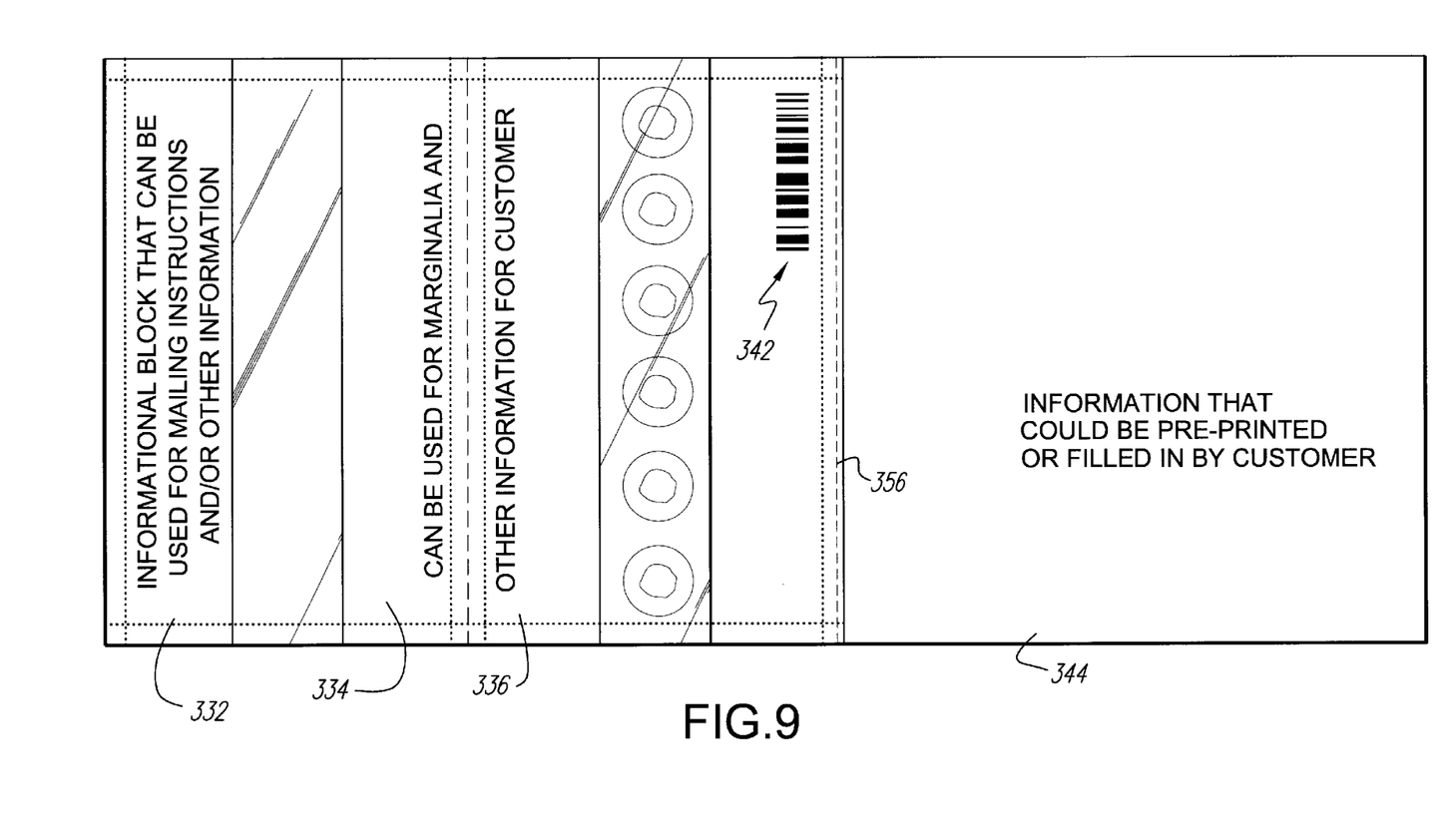
FIG. 9 is a rear or outside view of the sample receiving medical test form of FIG. 7.

As mentioned above, although a two panel form is illustrated in FIGS. 5 and 6, in accordance with a further alternate embodiment, a three or more panel form can be provided, to include additional informational material for the medical professional and/or the patient. An example of such a multi-panel form is illustrated in FIGS. 7–9. In this embodiment, a form 300 generally corresponding to the form illustrated in FIGS. 5 and 6 is side stick secured to an information bearing paper stock material 344 to define a medical test form 346. To side stick the plastic sheet and the web of paper stock, the web and the sheet are glued together along a longitudinal strip with enough overlap on each side to prevent exposure of adhesive 354.

Panels 302 and 304 generally correspond to the first and second panels 202,204 of the embodiment of FIGS. 5 and 6, described above. In the illustrated embodiment, however, a fourth adhesive strip 348 is provided for peripherally securing to the sample bearing panel 304. Accordingly, perforation lines 350,352 are further defined on the respective panels to facilitate access to the sample bearing media at the testing facility. The third panel 344 which is secured with adhesive 354 to the edge of the second panel 304 may be separated from the sample carrying panel by tearing along line of weakness 356, which may be a perforated line and which is disposed in parallel to the perforated line 318. Instructional materials may be provided to inform the patient how to secure a biological sample and apply the same to the sample receiving material segments 332, and how to prepare the form for mailing. Thus, once the panels 302,304 have been secured together to define the mailer, the mailer may be separated from the informational panel 344 by tearing along line 356. A bar code 340,342 is advantageously provided on the informational panel and mailer, respectively, to identify the corresponding medical test form and biological sample. Indeed, as will be understood, the three part form of FIGS. 7–9 has the advantage that all patient identifying information can be preserved on the informational panel, to thereby facilitate anonymous testing, identified only by the bar code information.

The folded and sealed biological sample containing section 300 of the form may be deposited in an outer envelope for transmission to the medical facility, in view of the transparent segments 226,228 which reveal the applied sample.

With reference to FIG. 9, portions of the back face of the panels 302 and 304 are coated and/or treated so as to be suitable for receiving preprinted information thereon, as described above with reference to FIGS. 5 and 6. The plastic substrate may be printed with a laser receptive topcoat and then laser printed in advance of side stick to panel 344 or thereafter as deemed necessary or desirable. As shown, one printable region 332 may be provided as an information block for mailing instructions and/or other information for the customer. Another section or sections 334,336 can be used for marginalia and/or other information for the customer as to how the form is used, folded and sealed. Finally, the back surface of the panel 344 may include a further information area that can be preprinted or filled in by the customer.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A medical test form comprising a sample carrier assembly having a sample receiving material secured to a first surface thereof, said sample carrier assembly including a back panel for covering a back surface of said sample receiving material and further including a protective sheet hingedly coupled to said back panel for selectively overlying a top surface of said sample receiving material whereby said sample receiving material is selectively sandwiched between and protected by said protective sheet and said back panel.

2. A medical test form as in claim 1, wherein at least one of said protective sheet and said back panel has adhesive material applied to at least a portion of a periphery thereof for selectively adhering said protective sheet in parallel relation to said back panel.

3. A medical test form as in claim 2, wherein said protective sheet and said back panel generally correspond in size and shape.

4. A medical test form as in claim 3, wherein said protective sheet and said back panel are hingedly coupled along mutually adjacent side edges thereof.

5. A medical test form as in claim 1, further comprising an informational panel secured to a side edge of said back panel, a line of weakness being defined at or adjacent a juncture of said back panel and said informational panel for disengaging said back panel and said informational panel.

6. A medical test form as in claim 2, further comprising an informational panel secured to a side edge of said back panel, a line of weakness being defined at or adjacent a juncture of said back panel and said informational panel for disengaging said back panel and said informational panel.

7. A medical test form as in claim 1, wherein said sample carrier assembly comprises a plurality of panels coupled end to end, one of said plurality of panels defining a sample receiving material carrying panel, said sample receiving material carrying panel including said back panel.

8. A medical test form as in claim 7, wherein said back panel comprises a tab component defined in said sample receiving material carrying panel.

9. A medical test form as in claim 8, wherein the sample receiving material is disposed in a sample receiving sub-assembly including a cover member and a backing member, with said sample receiving material disposed therebetween, said cover member and said backing member each having at least one hole defined therethrough for exposing said sample receiving material, said holes being mutually aligned with each other and with said tab component.

10. A medical test form as in claim 9, wherein said protective sheet comprises a top protective layer of said sample receiving sub-assembly, said protective sheet being adhesively secured to said cover member.

11. A medical test form as in claim 7, wherein said back panel is secured to a rear face of said sample receiving material carrying panel and said sample receiving material is secured to a front face of said sample receiving material carrying panel, and wherein said sample receiving material carrying panel has at least one hole defined therethrough for exposing said sample receiving material to said back panel.

12. A medical test form as in claim 1, wherein said sample receiving material is secured substantially directly to said back panel with an adhesive material.

13. A medical test form as in claim 12, wherein at least a portion of said back panel is transparent.

14. A medical test form as in claim 12, wherein at least a portion of said protective sheet is transparent.

15. A medical test form as in claim 1, wherein said protective sheet and said back panel comprise first and second panels of a three panel carrier substrate, the panels of said substrate being disposed end to end to define a substantially continuous web, with at least one line of weakness being defined between adjacent said panels for at least one of folding and severing said web.

16. A medical test form as in claim 1, wherein the sample receiving material is disposed in a sample receiving sub-assembly including a cover member and a backing member, with said sample receiving material disposed therebetween, at least said cover member having at least one hole defined therethrough for exposing said sample receiving material to receive a biological sample.

17. A medical test form as in claim 16, wherein said protective sheet comprises a top protective layer of said sample receiving sub-assembly, said protective sheet being adhesively secured to said cover member.

* * * * *